US010088457B2

(12) United States Patent
Athenstaedt

(10) Patent No.: US 10,088,457 B2
(45) Date of Patent: Oct. 2, 2018

(54) LOW POLLUTANT DIALYSIS SOLUTION

(71) Applicant: Fresenius Medical Care Deutschland GmbH, Bad Homburg (DE)

(72) Inventor: Behnusch Athenstaedt, Sankt Wendel (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 260 days.

(21) Appl. No.: 14/901,542

(22) PCT Filed: Jun. 23, 2014

(86) PCT No.: PCT/EP2014/063163
§ 371 (c)(1),
(2) Date: Dec. 28, 2015

(87) PCT Pub. No.: WO2014/206938
PCT Pub. Date: Dec. 31, 2014

(65) Prior Publication Data
US 2016/0131616 A1 May 12, 2016

(30) Foreign Application Priority Data
Jun. 25, 2013 (EP) .................................... 13003223

(51) Int. Cl.
*G01N 30/72* (2006.01)
*G01N 30/00* (2006.01)
*G01N 30/06* (2006.01)
*G01N 30/54* (2006.01)
*G01N 30/88* (2006.01)
*B01J 20/281* (2006.01)
*B01J 20/28* (2006.01)
*B01J 20/32* (2006.01)
*B01D 15/00* (2006.01)
*A61L 2/00* (2006.01)
*A61L 2/28* (2006.01)
*A61M 1/16* (2006.01)
*A61M 1/28* (2006.01)
*G01N 30/56* (2006.01)

(52) U.S. Cl.
CPC ............ *G01N 30/06* (2013.01); *A61L 2/0023* (2013.01); *A61L 2/28* (2013.01); *A61M 1/1654* (2013.01); *A61M 1/287* (2013.01); *B01J 20/3204* (2013.01); *B01J 20/3272* (2013.01); *G01N 30/54* (2013.01); *G01N 30/7206* (2013.01); *G01N 2030/567* (2013.01); *Y10T 436/24* (2015.01); *Y10T 436/255* (2015.01)

(58) Field of Classification Search
CPC ...... A61L 2/0023; A61L 2/28; A61M 1/1654; A61M 1/287; B01J 20/3204; B01J 20/3272; G01N 2030/567; G01N 30/06; G01N 30/54; G01N 30/7206; G01N 1/28; Y10T 436/24; Y10T 436/25; Y10T 436/25375; Y10T 436/255
USPC .......... 436/161, 173, 174, 177, 178; 422/89, 422/527; 424/680; 73/23.41, 863.12
See application file for complete search history.

(56) References Cited

U.S. PATENT DOCUMENTS

| 8,192,692 B2* | 6/2012 | Wohleb ............... B01L 3/50825 422/161 |
| 2011/0023711 A1* | 2/2011 | Sato ........................ B01J 20/08 95/90 |
| 2014/0356976 A1* | 12/2014 | Wohleb .................... G01N 1/34 436/178 |

FOREIGN PATENT DOCUMENTS

| EP | 1039288 | 9/2000 |
| JP | 2010217197 | 9/2010 |
| WO | WO 91/15745 | 10/1991 |

OTHER PUBLICATIONS

Meng et al. Determination of phthalate esters in polyvinyl chloride infusion bag by stir bar sorptive extraction combined with GC. Journal of Seperation Science, Dec. 7, 2012, vol. 35, No. 24, pp. 3486-3491.
Sun et al, Determination of phthalat esters in polyvinyl chloride infusion bag by stir bar sorptive extraction combined with GC. Journal of Separation Science, vol. 35, No. 24, Dec. 7, 2012, pp. 3486-3491.
Cacho et al. Stir bar sorptive extraction coupled to gas chromatographymass spectrometry for the determination of bisphenols in canned beverages and filling liquids of canned vegetables. Journal of Chromatography, vol. 1247, May 20, 2012, pp. 146-153.
Yamaguchi et al. A cost effective, sensitive, and environmentally friendly sample preparation method for determination of polycyclic aromatic hydrocarbons in solid samples. Journal of Chromatography, vol. 1217, No. 44, Oct. 29, 2010, pp. 6816-6823.
Sanchez-Rojas et al. A Review of Stir Bar Sorptive Extraction. Chromatographia: An internation Journal for Rapid Communication in Chromatography, vol. 69, No. 1, Jun. 25, 2008, p. 79-94.

(Continued)

*Primary Examiner* — Maureen Wallenhorst
(74) *Attorney, Agent, or Firm* — Jacobson Holman, PLLC.

(57) ABSTRACT

A method for the determination of pollutants and leachables in a dialysis solution by stir bar sorptive extraction involves conditioning a sorptive material-coated stir bar, stirring the dialysis solution with the conditioned stir bar, desorbing of pollutants and leachables from the coated stir bar, and analyzing the desorbed pollutants and leachables by gas chromatography-mass spectrometry (GC-MS).

3 Claims, No Drawings

(56) References Cited

OTHER PUBLICATIONS

Behnusch Athenstädt. Development of GC-MS methods for the identification and quantification of leachables from plastic packaging in dialysis solution. Jun. 23, 2013, pp. 1-205, XP55083783, http://duepublico.uni-duisburg-essen.de/servlets/DocumentServlet?id=31436&lang=en.
Conor T. Hanrahan, et al. The challenges of heat sterilization of peritoneal dialysis solutions: Is there an alternative? Advances in Peritoneal Dialysis, vol. 28, Jan. 1, 2012, pp. 126-130, XP055349777, http://www.advancedinpd.com/ady12/Part3/126.pdf.
Guogang, Li. Progress report on Science and Technology of Environmental Monitoring: Symposium of The Ninth National Environmental Monitoring (vol. 1). China Environmental Science Press, p. 373-374, Aug. 2009.

\* cited by examiner

LOW POLLUTANT DIALYSIS SOLUTION

TECHNICAL FIELD

The present invention relates to a low pollutant dialysis solution and a method for analyzing a dialysis solution. The present invention further relates to methods of validating dialysis solution batches, primary packaging material and the optimization of sterilization procedures.

BACKGROUND ART

Packaging made of plastics frequently protect pharmaceutical solutions such as dialysis solutions from changes of their composition for example by outgassing of solution components on the one hand and from outside factors like humidity or oxygen on the other hand. Thus plastic packing materials improve the shelf life and stability of these products during storage. Furthermore plastic packaging has for example the advantage of a lower weight and an easier handling compared to glass bottles. In addition their properties such as stability, elasticity or permeability to gases can be matched to particular requirements within a wide range of possibilities. On the other hand plastics harbor the risk that low molecular weight substances, such as monomers, oligomers, plasticizers or catalyst components might migrate from the packaging into the pharmaceutical and pose a safety risk to patients this way. These considerations are especially problematic for pharmaceutical liquids due to the direct contact of the packaging with the product and the likelihood that soluble substances derived from the packaging are rapidly diffusing into the solution.

Common leachables in plastic material are phthalates or phthalate esters, which are esters of phthalic acid and mainly used as plasticizers to soften polyvinyl chloride (PVC). In studies of rodents exposed to certain phthalates, high doses have been shown to change hormone levels and cause birth defects. Examples of phthalates are diethylphthalate (DEP), di-iso-butylphthalate, di-butylphthalate (DBP) and dicyclohexylphthalate (DCHP).

Oleamide and erucamide fatty acid derivatives are the most common slip agents used in polyethylene film. Other slip agents are decanamide, dodecanamide, hexadecanamide, stearamide.

2-t-butyl-, 4-t-butyl and 2,4-Di-t-butyl phenol are monomers of tertiary butyl phenol formaldehyde resins and may cause allergic reactions.

Divinylbenzene (DVB) is a mixture of 1,3- and 1,4-Divinylbenzene. Divenylbenzene is used as a cross-linker in styrene polymers. It is known to be a strong irritant and slightly genotoxic.

Since the end of 2005, the European Medicines Agency (EMEA) has consequently required the exact identification and quantification of migrating substances to comply with the Guideline on Plastic Immediate Packaging Materials (CPMP/QWP/4359/03). This guideline demands a toxicological assessment of all migrating substances regardless of their amount. Because it seems reasonable to assume that below a certain level a substance is of no risk to human safety, the product quality research institute (PQRI, Arlington, Va., USA) proposed a safety concern threshold (SCT) in response to this guideline. A SCT value of 150 ng/day was recommended basing on a scientific rationale for orally inhaled and nasal drug products (OINDP) as a threshold below which no toxicological qualification for a leachable is necessary. The parenteral and ophthalmic drug products (PODP) leachables and extractables working group of the PQRI advised to adopt this value for pharmaceutical solutions, which includes dialysis solutions used for peritoneal dialysis (PD) and hemodialysis (HD) as well. PD and HD are treatment modalities for patients with an acute or chronic renal failure.

Solutions used for the peritoneal dialysis place the highest demands on the quantification of leachables. Usually a volume of 2 liter dialysis solution is introduced in the abdomen of the patient. It remains there for about 5 hours and is finally replaced with fresh solution. This results in a total volume of about 10 liters per day. The total volume doubles if automated solution changers are used. Therefore the determination of the SCT of 150 ng/day requires an analytical method with a limit of detection (LOD) of 15 ng/L (10 L dialysis solution per day) or even 7.5 ng/L (20 L per day). For hemodialysis solutions, or hemofiltration solutions to be more precisely, a LOD of 35 ng/L is required. This value was calculated by assuming three hemofiltration treatments per week with a 4 hour duration and a final exchanged volume of 10 L per treatment.

Analytical methods for the determination of leachables in pharmaceutical solutions below the SCT have to fulfill at least two requirements. Firstly they must be able to quantify a possibly large number of compounds in a mixture simultaneously and secondly they have to be sensitive enough for trace analysis in regard to their limit of detection (LOD) and limit of quantification (LOQ), respectively.

A very common technique used for this purpose is liquid-liquid extraction (LLE) followed by a gas chromatographic (GC) separation of the extracted sample. The extraction of the aqueous sample with an organic solvent is necessary especially for the enrichment of leachables and to allow the injection into the GC column. Typically, 100 g of an aqueous sample is mixed with 4 g of chloroform for 1 h. The main disadvantages of LLE are its time-consumption, the high costs and the usage of large volumes of potentially toxic solvents, which are hazardous to health as well as to environment. The limit of quantification of LLE depends on the specific compound and is between 10 µg/kg and 250 µg/kg, which is not sufficient to meet the requirements of SOT.

WO 91/15745 discloses the method of solid-phase microextraction (SPME) which offers an improved limit of quantification. This method uses fibers coated with polydimethylsiloxane (PDMS), which are placed in a needle of a syringe-like arrangement to extract and enrich non-polar compounds from an aqueous sample. The fiber has only a very limited absorption capacity for substances which are to be examined and, moreover, is only dipped into the stirred carrier fluid, so that consequently the sensitivity of the analysis itself leaves something to be desired if the coated fiber is vibrated.

EP 1 039 288 discloses a modified SPME setup. This method uses a PDMS coated stir bar and is, therefore, called stir bar sorptive extraction (SBSE).

There is still a demand for an analytical method to determine leachables and pollutants in medical solutions like, e. g., dialysis solutions, which meets the requirements of SOT.

SUMMARY OF INVENTION

One object of the invention is to provide an analytical method with significantly improved sensitivity to substances in medical solutions originating from packaging material.

The method of present invention may be useful to validate a batch for distribution of a dialysis solution in a polymer container, e.g., dialysis solutions in a multi-chamber bag. In a validation procedure the dialysis solution is filled into packaging material and thermally sterilized. A number of containers of a batch are sampled and the dialysis solution is analyzed using the method of the present invention. The total amount of a pollutant or leachable in this sample is determined. The batch is released for distribution only if the sample of the batch contains less than 150 ng/L by weight of said pollutant or leachable.

In one embodiment of the present invention the solution is analyzed for oleamide and erucamide. The batch is released for distribution only if the sample of the batch contains less than 150 ng/L of oleamide or erucamide.

In one embodiment of the present invention the solution is analyzed for 1,3- and 1,4-divinylbenzene. The batch is released for distribution only if the sample of the batch contains less than 150 ng/L of said divinylbenzenes.

In one embodiment of the present invention the solution is analyzed for diethylphthalate (DEP), di-iso-butylphthalate, di-butylphthalate (DBP) and dicyclohexylphthalate (DCHP). The batch is released for distribution only if the sample of the batch contains less than 150 ng/L of said phthalates.

The method of present invention may also be useful to validate packaging material for medicinal products, e.g., dialysis solutions. In a validation procedure a dialysis solution is filled into packaging material and thermally sterilized under conditions which are equal to the conditions of thermal sterilization in commercial production. In one embodiment of the present invention the sterilization conditions in the validation procedure exceed the conditions of thermal sterilization in commercial production. The temperature is increased by at least 10%, preferably more than 20%, and the holding time by at least 20%, preferably at least 50%. For example, if the commercial heat sterilization procedure comprises a holding time of at least 15 minutes at 121° C., the method of the present invention comprises a holding time of at least 60 minutes at 131° C.

After sterilization, the dialysis solution is analyzed using the method of the present invention. The total amount of a pollutant or leachable in this sample is determined. A packaging material is approved for use in production only if the sample of the batch contains less than 150 ng/L by weight of said pollutant or leachable.

In one embodiment of the present invention the solution is analyzed for oleamide and erucamide. The packaging material is approved for use in production only if the sample of the batch contains less than 150 ng/L of oleamide or erucamide.

In one embodiment of the present invention the solution is analyzed for 1,3- and 1,4-divinylbenzene. The packaging material is approved for use in production only if the sample of the batch contains less than 150 ng/L of said divinylbenzenes.

In one embodiment of the present invention the solution is analyzed for diethylphthalate (DEP), di-iso-butylphthalate, di-butylphthalate (DBP) and dicyclohexylphthalate (DCHP). The packaging material is approved for use in production only if the sample of the batch contains less than 150 ng/L of said phthalates.

The method of the present invention may also be useful to optimize a sterilization procedure in order to limit the amount of pollutants leached from the packaging material into the solution. Medical solutions are typically sterilized by heat sterilization. To achieve sterility, a holding time of at least 15 minutes at 121° C. or 3 minutes at 134° C. is required. Additional sterilizing time is usually required for liquids.

Factors influencing the migration of leachables and pollutants from the packaging material into the solution are time and temperature. Elevated temperatures increase the rate of diffusion and thus the migration of pollutants from the packaging material into the solution. An unnecessarily prolonged sterilization time will lead to higher initial amount of pollutants while the microbial quality of the solution is not further improved.

In an experimental setup to optimize a sterilization procedure several samples are sterilized at various temperatures and/or for various periods of time. After sterilization, the dialysis solution is analyzed using the method of the present invention. The total amount of a pollutant or leachable in this sample is determined. A sterilization method is approved for use in production only if the sample of the batch contains less than 150 ng/L by weight of said pollutant or leachable.

The method of the present invention is therefore useful to optimize a sterilization procedure in order to limit the initial amount of pollutants leached from the packaging material into the solution, while at the same time to ensure a sufficient sterilization.

In one embodiment of the present invention the solution is analyzed for oleamide and erucamide. The sterilization method is approved for use in production only if the sample of the batch contains less than 150 ng/ of oleamide or erucamide.

In one embodiment of the present invention the solution is analyzed for 1,3- and 1,4-divinylbenzene. The sterilization method is approved for use in production only if the sample of the batch contains less than 150 ng/L of said divinylbenzenes.

In one embodiment of the present invention the solution is analyzed for diethylphthalate (DEP), di-iso-butylphthalate, di-butylphthalate (DBP) and dicyclohexylphthalate (DCHP). The sterilization method is approved for use in production only if the sample of the batch contains less than 150 ng/L of said phthalates.

Although the foregoing has been a description of preferred embodiments of the invention, it will be apparent to those skilled in the art that numerous variations and modifications may be made in the invention without departing from the scope as described herein. Other pollutants or leachables which may analyzed by the method of the present invention are: phenol, 2'-Hydroxyacetophenone, 2-tert-Butylphenol, 4-tert-butylphenol, 2,6-di-tert-butylphenol, 2,4-di-tert-butylphenol, bisphenol A (BPA), butylhydroxytoluene (BHT), cyclohexanol, 2-ethylhexanol, benzyl alcohol, dodecanol, octadecanol, undecane, 2-(2-butoxyethoxy)ethyl acetate, methyl-iso-butylketone (MIBK), cyclohexanone, toluene, ethylbenzene, styrene, benzaldehyde, 1,2-dicyanobenzene and chlorobenzene, 4-tert-amylphenol, 1,4-diacetylbenzene, decanamide, dodecanamide, hexadecanamide, stearamide and 4-methyl-2-heptanone, tetradecanamide, 5,5-dimethyl-2,4-hexandione, 1,3-diacetylbenzene and 2-ethylhexanoic acid, heptanoic acid, octanoic acid, decanoic acid, dodecanoic acid, tetradecanoic acid, hexadecanoic acid, octadecanoic acid, docosanoic acid and 3-(3,5-di-tert-butyl-4-hydroxyphenyl)-propionic acid.

For the detection of compounds in the ng/kg range a stir bar has be free of any background contamination. The conditioning of the stir bar is therefore a crucial parameter. Methods known in the art comprise a simple conditioning step such as heating the stir bars for a certain time at temperatures up to 300° C. It was found that this is procedure is insufficient.

Two different methods can be used to minimize background contamination. Both conditioning methods include at least one washing step in a 1:1 mixture of methanol and dichloromethane. Optionally, the stir bars can be placed in 6 mL of 1:1 mixture of methanol and dichloromethane and then sonicated for 15 min. This step can, optionally, be repeated 4 more times with a renewed washing solution. Afterwards the stir bars were dried under pure nitrogen at 30° C. for 30 min and then backed out at 300° C. for 4 hours. Subsequently the stir bars were allowed to cool down to room temperature under nitrogen.

The second conditioning procedure comprises the steps of stirring the stir bar in 6 mL of the cleaning solution comprising a mixture of methanol and dichloromethane for 4 hours and drying them as already described above. The cleaning solution comprises methanol and dichloromethane in a volume ratio of 3:1 to 1:3, preferably 2:1 to 1:2, most preferred 1:1.

This procedure may optionally be varied by exchanging the cleaning solution after 2 hours and additionally repeating the drying step twice.

The second conditioning procedure described above showed the lowest remaining contaminations and is therefore the preferred conditioning method.

The stirring or extraction time during extraction mainly influences the duration of the sample analysis. Thus a short time would be preferable. Contrary to this demand is the advantage of a longer stirring time, which ensures that equilibrium conditions are reached regarding the water-PDMS-partitioning of the solute. Typical extraction times are between 60 min and 24 h. The exact time until an equilibrium is reached depends e.g. on the diffusivity of the solute, on the phase ratio, the stirring speed, and the temperature.

The extraction time can be 30 min, 60 min, 120 min, 240 min, 360 min, 960 min and 1440 min. The preferred extraction time is about 240 min. After this period of time the equilibrium between PDMS and water is reached. A prolonged extraction does not increase the amount of substances adsorbed, but rather prolongs the overall analysis time.

It was surprisingly found that a prolonged extraction time may even be a disadvantage due to desorption of extracted compounds. This applies, e.g., for fatty acids. The concentration in the PDMS may decrease considerably for extraction times much longer than 240 min. Interestingly, the reduction of the extracted amount of acids by time has an inverse correlation with the number of carbon atoms and thus with the hydrophobicity and $K_{O/W}$ value, respectively. The decrease from 4 h to 24 h is more pronounced for dodecanoic acid, whereas nearly no change in target ion peak area was observed for the octadecanoic acid.

The stir bar dimensions, the PDMS volume and the sample volume directly influence the extraction efficiency. Both variables are connected via the partition coefficient as shown in the well-known formula (1):

$$K_{PDMS/Water} = \frac{c_{PDMS}}{c_{Water}} = \frac{m_{PDMS}}{m_{Water}} \cdot \frac{V_{Water}}{V_{PDMS}} = \frac{m_{PDMS}}{m_{Water}} \cdot \beta$$

The partition coefficient KPDMS/Water for the solute distribution in PDMS and water is defined as the ratio between the solute concentrations in PDMS ($c_{PDMS}$) and water ($c_{Water}$), which is equal to the mass ratio ($m_{PDMS}/m_{Water}$) times the phase ratio $\beta$. Commercially available stir bars have PDMS volumes of 23.5 μL (10 mm long stir bar with a 0.5 mm thick PDMS coating, herein after referred to as "10×0.5"), 47 μL ("20×0.5" stir bar), 63 μL ("10×1" stir bar) up to 126 μL ("20×1"). As higher PDMS volumes result in higher extraction values, the 20×1 stir bar is preferred.

Additionally, the thickness of the PDMS layer may have an effect on the extraction as it influences the kinetics of the absorption.

The extraction efficiency of polar solutes is enhanced by salting out. The addition of salt, preferably sodium chloride, increases the ionic strength. This reduces the solubility of organic compounds and increases their partition coefficient between PDMS and water. Consequently, the extraction yields increase.

As a standard dialysis solution comprises a wide variety of different substances ranging from the very polar region (log $K_{O/W}$=-2.9 for the dissociated form of the ethylhexanoic acid) to the apolar region (log $K_{O/W}$=8.4 for erucamid) salting out may strongly influence the extraction.

Sodium chloride may be added to a dialysis solution sample in amounts resulting in a sodium chloride concentration of 120 g/L, 240 g/L, 320 g/L, 340 g/L or 360 g/L. The addition of 9 g sodium chloride to 25 mL of a dialysis solution sample results in a salt concentration of 360 g/L which is above the water solubility limit of sodium chloride (359 g/L at 20° C.). This results in a saturated solution. It is, therefore, preferred to adjust a sodium chloride concentration which is 90 to 99% of saturation, more preferred 95 to 99% of saturation. This corresponds to a sodium chloride concentration of about 323 g/L, about 341 g/L or about 355 g/L.

While the addition of salt affects the partition coefficient of the solute and is thus a thermodynamic factor, the stirring speed affects the kinetics of the extraction. Typical stirring rates are between 600 rpm and 1200 rpm, whereas a higher stirring speed increases the transfer coefficient from the aqueous solution into the PDMS, because it minimizes the thickness of the diffusion layer. This thin layer, which is also called concentration boundary layer, is a region close to the PDMS surface, where the concentration of the analytes is lower than in the bulk solution. This decreases the concentration gradient between the PDMS and its direct surrounding. Using high stirring speeds minimizes the thickness of this boundary layer and thus minimizes the resistance for the solute transport into the PDMS. Stirring rates of 1000 to 1200 rpm or 1100 to 1200 rpm are preferred.

For the analysis via GC the analytes were thermally desorbed from the PDMS. Here two parameters—time and temperature—have the major influence on the desorption efficiency.

There is no significant difference between 250° C. and 280° C., but for most of the compounds a desorption temperature of 280° C. gave slightly higher signals. No thermal degradation of substances was observed. As the higher temperature also minimizes carry over effects, a temperature of 280° C. is preferred.

The desorption time may be 2.5 min, 5 min, 7.5 min or 10 min at a constant desorption temperature of 280° C. A 50% increase in the target ion peak area was observed when increasing the time from 2.5 min to 10 min. Therefore, a 10 min desorption time is preferred.

The sample heat up rate may be between 12° C./s and 16° C./s. While a faster heat up rate leads to faster desorption a slower heat up leads to about two times higher signals and was thus preferred for this method.

EXAMPLES

The following 52 compounds were used as analytes:

Phenol, 2'-Hydroxyacetophenone, 2-tert-Butylphenol, 4-tert-butylphenol, 2,6-di-tert-butylphenol, 2,4-di-tert-butylphenol, bisphenol A (BPA), butylhydroxytoluene (BHT), cyclohexanol, 2-ethylhexanol, benzyl alcohol, dodecanol, octadecanol, diethyl-phthalate (DEP), di-isobutylphthalate, di-butylphthalate (DBP), dicyclohexylphthalate (DCHP), undecane, 2-(2-butoxyethoxy)ethyl acetate, methyl-iso-butylketone (MIBK), cyclohexanone, toluene, ethylbenzene, styrene, divinylbenzene (DVB), benzaldehyde, 1,2-dicyanobenzene and chlorobenzene, 4-tert-amylphenol, oleamide, erucamide and 1,4-diacetylbenzene, decanamide, dodecanamide, hexadecanamide, stearamide and 4-methyl-2-heptanone, tetradecanamide, 5,5-dimethyl-2,4-hexandione and 1,3-diacetylbenzene.

The standard stock solution was prepared by dissolving these substances in ethanol with a final concentration of 3 mg/kg for each of the analytes.

A second standard stock solution in ethanol was prepared for ten carboxylic acids with a concentration of about 6 mg/kg: 2-ethylhexanoic acid, heptanoic acid, octanoic acid, decanoic acid, dodecanoic acid, tetradecanoic acid, hexadecanoic acid, octadecanoic acid, docosanoic acid and 3-(3,5-di-tert-butyl-4-hydroxyphenyl)-propionic acid.

Both stock solutions were stored in the darkness at room temperature.

A solution of phenanthrene-$D_{10}$ (Sigma Aldrich) at 2 mg/kg in ethanol (p.a., Merck KGa) was used as an internal standard. All samples were spiked with this standard, to have a final concentration of 75 µg/kg phenantrene-$D_{10}$.

The PDMS coated Twister™ stir bars were purchased from Gerstel GmbH (Mülheim, Germany). The stir bars were cleaned and conditioned before every measurement by stirring them in 6 mL of a 50:50 mixture of methanol and dichloromethane for 4 hours, with a renewal of the solvents after 2 hours. Afterwards, the stir bars were dried under pure nitrogen at 30° C. for 30 min and then conditioned at 300° C. for 4 hours. The stir bars were allowed to cool down to room temperature for 4 hours under nitrogen. The heat conditioning procedure with the additional cool down to room temperature was repeated once more.

One peritoneal dialysis solution was analyzed. The dialysis solution was supplied in dual-chamber 5 L bags. Prior to analysis the contents of both chambers were thoroughly mixed directly before the measurement as described in the respective instructions of use. Afterwards four samples with 25 mL were extracted as described in the following.

A sample volume of 25 mL was placed in glass head space vials with a nominal volume of 25 mL. Then 8.5 g sodium chloride and 100 µL of the phenantrene-$D_{10}$ solution were added and 2 cm long PDMS stir bars with a 1 mm thick PDMS coating (=126 µL PDMS phase volume) were placed into the vials. Subsequently the vials were sealed with a crimp cap. The extraction was performed for 4 h at a stirring speed of 1100 rpm at 25° C. Afterwards, the stir bars were removed with a magnetic stir bar retriever, rinsed with water and shortly purged with nitrogen to remove the water from the surface. Rinsing with water does not influence the analytes, because they are absorbed within the PDMS and are not located on the surface. Finally, the stir bars were transferred into a desorption tube and placed on the auto sampler tray. These desorption tubes were cleaned after every three measurements by rinsing them first with water and afterwards with acetone. Subsequently they were dried over night at 70° C.

The entire stir bar handling was done with tweezers, to avoid possible contamination by direct contact.

The phenanthrene-$D_{10}$ was used to spike every sample and served therefore as a control compound to assure an accurate and error free sample extraction procedure. Deviations from the usually obtained target ion peak area for phenanthrene-$D_{10}$ point to a probably not correct stirring process during extraction or to an advanced aging of the stir bar.

The GC/MS measurements were performed using a GC 7890 system from Agilent equipped with a thermal desorption unit "TDU" (Gerstel) and a cold injection system "CIS" (Gerstel). Additionally a multipurpose autosampler "MPS" (Gerstel) was used to introduce the stir bars into the TDU. The desorption took place in solvent vent mode at 280° C. for 10 min. Helium 5.0 was used to transfer the analytes into the CIS where they were cryo-focused at −120° C. Finally the CIS was heated up to 280° C. at a speed of 12° C./s and the analytes were injected into the GC column. The helium carrier gas had a constant flow rate of 1 mL/min. The temperature program used for chromatographic separation involved a one minute waiting time at 50° C. after the injection. Afterwards the temperature was increased from 50° C. to 150° C. at a rate of 10° C./min, and then maintained at this level for 5.5 min before increasing the temperature further at a rate of 50° C./min rate to 300° C., and then maintaining the temperature at this level for 10 min. The ion source was held at a temperature of 270° C. The detector was an Agilent 5973 quadrupole mass spectrometer (MS) with an electron impact (EI) source and was used in scan mode. Mass-to-charge ratios (m/z) were recorded at values between 25 and 700. The column used was a Zebron (ZB-50) capillary column (length 30 m, diameter 0.25 mm, film thickness 0.50 µm, stationary phase: 50% diphenyl polysiloxane, 50% dimethyl polysiloxane) purchased from Phenomenex (Aschaffenburg, Germany).

The sample of the peritoneal dialysis solution exhibited a broad spectrum of leachables, which represented about 75% of the components used for the standard stock solutions. This finding proved the practical relevance of the standard solution composition. No unknown substances were detected in any of the solutions during the GC-MS analysis. Most of the leachables were found in concentrations between 1 µg/kg and 10 µg/kg. Some of the leachables (diethyl phthalate, dibutyl phthalate, oleamide and erucamide) were found to be in the range down to 0.1 µg/kg. No dicyclohexylphthalate and no BPA were detected.

The invention claimed is:

1. Method for determination of pollutants and leachables in a dialysis solution by stir bar sorptive extraction comprising the steps of
   conditioning a stir bar coated with a sorptive material by washing the coated stir bar in a mixture comprising methanol and dichloromethane,
   adding sodium chloride at a concentration of at least 90% saturation to the dialysis solution,
   stirring the dialysis solution with the conditioned coated stir bar, followed by
   desorption of pollutants and leachables from the coated stir bar, and
   analysis of the desorbed pollutants and leachables by gas chromatography-mass spectrometry (GC-MS).

2. Method of claim 1, wherein the conditioning step additionally comprises ultrasonic treatment.

3. Method of claim 1, wherein the sorptive material coating the stir bar is polydimethylsiloxane (PDMS).

* * * * *